(12) United States Patent
Reiss

(10) Patent No.: US 6,488,628 B1
(45) Date of Patent: Dec. 3, 2002

(54) METHOD FOR ULTRASONICALLY PROFILING THE DISTRIBUTION OF AN ADMINISTERED MEDICAMENT

(75) Inventor: Robert E. Reiss, La Jolla, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/920,551

(22) Filed: Jul. 31, 2001

(51) Int. Cl.⁷ ................................................. A61B 8/00
(52) U.S. Cl. ........................................ 600/438; 600/439
(58) Field of Search .................. 604/890.1, 20–23; 128/912, 913; 600/438, 439; 601/2–4

(56) References Cited

U.S. PATENT DOCUMENTS

| | | | |
|---|---|---|---|
| 5,016,615 A | * 5/1991 | Driller et al. ............ 604/890.1 |
| 5,053,033 A | 10/1991 | Clarke |
| 5,199,939 A | 4/1993 | Dake |
| 5,411,466 A | 5/1995 | Hess |
| 5,540,659 A | 7/1996 | Teirstein |
| 5,562,594 A | 10/1996 | Weeks |
| 5,615,680 A | * 4/1997 | Sano ......................... 600/454 |
| 5,624,372 A | 4/1997 | Liprie |
| 5,643,171 A | 7/1997 | Bradshaw |
| 5,683,345 A | 11/1997 | Waksman |
| 5,688,220 A | 11/1997 | Verin |
| 5,840,008 A | 11/1998 | Klein |
| 5,863,284 A | 1/1999 | Klein |
| 6,024,690 A | 2/2000 | Lee |
| 6,033,357 A | 3/2000 | Ciezki |
| 6,086,573 A | * 7/2000 | Siegel et al. ................ 604/507 |
| 6,126,600 A | * 10/2000 | Oxaal et al. ................ 600/439 |
| 6,245,747 B1 | * 6/2001 | Porter et al. ............... 424/9.52 |

* cited by examiner

Primary Examiner—Francis J. Jaworski
(74) Attorney, Agent, or Firm—Kenyon & Kenyon

(57) ABSTRACT

A method for profiling an infusion of a medicament into the wall of an artery involves inserting an intravascular ultrasound device into the artery and advancing it to the location of the infusion. A pullback device withdraws the intravascular ultrasound device from the artery, pausing at predetermined axial sites along the location of the infiltrated medicament to image the infusion profile at each site. A computer then compiles the individual site profiles to produce three dimensional images indicating the extent of infiltration of the medicament into the tissue surrounding the artery.

16 Claims, 2 Drawing Sheets

METHOD FOR ULTRASONICALLY PROFILING THE DISTRIBUTION OF AN ADMINISTERED MEDICAMENT

FIELD OF THE INVENTION

The present invention relates generally to imaging procedures. More specifically, the present invention relates to methods and systems for imaging tissues surrounding arteries. The present invention is particularly, though not exclusively, useful for using intravascular ultrasound to profile an infiltration of a medicament into the tissue surrounding an artery.

BACKGROUND OF THE INVENTION

Angioplasty is a widely used procedure for treating a stenosis within a body vessel such as a human artery. Although the angioplasty procedure is generally successful in dilating the lumen of the vessel, and thereby allowing increased blood flow through the vessel, often times a restenosis occurs soon after the angioplasty procedure. It is widely recognized that the body's response (inflammation). to the tissue damage that occurs during an angioplasty procedure contributes to the occurrence of a restenosis. Several medicaments, however, are known to be efficacious for the prevention of a restenosis if properly delivered near the site of the inflammation. To that end, devices that are capable of penetrating the wall of a vessel with a dispenser and releasing a medicament into the vessel wall have been developed. For example, U.S. Pat. No. 5,713,863 which issued to Vigil et al. for an invention entitled "Catheter With Fluid Medication Injectors," and which is assigned to the same assignee as the present invention, discloses such a device. It is the case, however, that these intravascular infusion devices can be used to deliver medicaments for prevention of restenosis as well as for other treatment and diagnostic purposes.

There are various forms of tissue injury that can result from an intravascular procedure, any one of which will trigger an inflammation response. As indicated above, such an inflammation response is widely recognized to contribute to the restenosis of the vessel. It is also known that this inflammation response will cause localized changes near the injured tissue including increased permeability and increased blood flow. This localized increase in blood flow and permeability will generally increase the dispersion rate of medicaments released near an injury in a vessel wall.

For a medicament to be effective in preventing a restenosis it must be delivered to a prescribed area and in a prescribed dosage. To do this efficiently, the size, shape and location of the prescribed treatment area must be determined, and this will depend on the amount and location of tissue injury. Also, the dispersion rate of the medicament will be affected by the amount of inflammation, the type of medicament, and the amount of medicament released. Due to the many variables involved, it would obviously be helpful to know exactly where the medicament has dispersed into tissue after it has been administered.

It happens that results of an intravascular infusion procedure are not the same from patient to patient. This may be due to a variety of reasons. One possible reason is the anatomical differences between patients. The differing results can also be due to different degrees of inflammation of the tissues, as discussed above. In any event, the actual distribution of the medicament has been a matter of estimate, based on clinical results. Heretofore, there has been no reliable in-vivo method to ascertain the success of an intravascular infusion procedure. Thus, it can be appreciated that it would be beneficial to know whether the medicament actually reached the target tissue. It would also be desirable to know whether the infused medicament is uniformly distributed in the target area. Of further interest to a clinician would be the concentration of the infused medicament in the tissues surrounding the arterial wall.

Information regarding the condition of tissues inside a patient can be obtained using diagnostic radiology. In particular, diagnostic ultrasound techniques can give information about tissue condition by differentiating between tissues at their anatomic boundaries inside the patient. Specifically, this happens as transmitted ultrasound waves reflect back to the transducer from these boundaries. The amplitude of the reflected ultrasound waves is then displayed as different shades of gray. Thus, anatomic structures with different acoustic density will be portrayed with different brightness. The introduction of a medicament into a tissue, however, changes its videodensitometry. Importantly, an ultrasonic image can show this difference.

Ultrasound technology is now available which will produce an inside view of an artery. Specifically, intravascular ultrasound, or IVUS, incorporates an ultrasound head within: a balloon catheter which can be used to obtain a cross sectional image of an artery. This image will also include the tissue that is surrounding the artery. An example of the use of IVUS can be found in the detection of plaque inside artery walls. Another example is the use of IVUS to determine the position and orientation of a probe during a procedure, using perivascular structures as landmarks.

In light of the above, it is an object of the present invention to provide a reliable method for profiling an infiltration of a medicament into the tissue surrounding an artery. Another object of the present invention is to provide a method and a system to determine the extent of the infiltration of the medicament into an arterial wall of a patient. A further object is to provide a system for quantitatively evaluating the distribution of the medicament in the tissue surrounding the artery. Yet another object of the present invention is to provide a method for profiling the infiltration of a medicament into the tissue surrounding the artery that is easy to perform, is safe, and is comparatively cost effective.

SUMMARY OF THE PREFERRED EMBODIMENTS

The present invention is directed to a method for determining the extent of an infiltration of a medicament into an arterial wall of a patient. Essentially, this is a two-step process. First, the medication is administered. Second, the extent of medication infiltration is determined. In accordance with the present method, a balloon catheter infusion device containing the fluid medicament is positioned in the artery of the patient at the treatment site. Upon being so positioned, the device then injects the medicament from inside the lumen of the artery into the wall of the artery. As the medicament is released, it infiltrates into the tissue surrounding the artery. It is anticipated that this procedure can be accomplished either at only one treatment site or repeated at a number of locations along the wall of the artery. This, of course depends on the pathology of the artery. In detail, when multiple infusions are to be performed, the infusion device is first advanced to a position in the artery that is most distal from the point of entry for the device. The device is then gradually pulled back through the artery, and the medicament is injected into selected sites along the arterial wall. When the infusion process is completed, the balloon catheter housing the infusion device is withdrawn from the artery.

In accordance with the present invention, after the infusion device has been withdrawn, another catheter is inserted into the lumen of the artery. This second catheter houses an intravascular ultrasound device (IVUS) of a type well known in the pertinent art. The IVUS is then advanced to the location of the infusion that is most distal from the point of entry of the device. The ultrasound is activated, and it begins imaging the arterial wall at a start point.

From this start point, the device is incrementally withdrawn, through the artery. This is preferably done using a motorized pullback device which will stabilize the IVUS in an axial orientation as it takes images of the artery between its incremental movements through the artery.

As the IVUS is thus pulled back along the axis of the artery, it creates a series of images at predetermined or preselected positions in the artery.

Each image, thus created, will represent the extent of medicament perfusion at a specific axial position in the artery. Once the ultrasound has created a profile of the tissue surrounding the artery, at the various axial positions in the artery, the IVUS is removed from the artery. It is known that IVUS, in general, provides a cross sectional view of the inside of an artery and the tissues immediately surrounding the artery. Thus, these images that are created at the series of specific axial sites in the artery, will each include a radial and an azimuthal dimension. The present invention envisions a computer/ultrasound interface that is capable of combining all of these images to produce a three dimensional image of the tissue surrounding the artery.

In operation, the specific sites for creating images with the IVUS are based on the location of the infusion. As indicated above, it is contemplated that multiple images will be created at a given infusion site. It then follows that, if a medicament has been infused at more than one site, each infusion site will be imaged a number of times. Further, at each infusion site it is desirable to know the boundaries of the perfusion or infiltration of a medicament. For diagnostic purposes, these boundaries will include a first end, the radial extent of the perfusion through an azimuthal range, and a second end. These measurements will then represent the extent of penetration of the medicament into the tissue surrounding the artery. Preferably, a minimum of three sites along the arterial wall at each infusion site will be selected for imaging with the IVUS. This determination will be repeated for each infiltration that has been performed.

In detail, and taking into account that IVUS generates images from specific axial positions in the artery, radial and azimuthal dimensions can be ascertained for each position. These dimensions correspond to the boundaries of the perfusion at each position. Beginning at a first position, the start point, a first image is created by the IVUS in a manner known in the art. When a clinician determines that this image represents the distal point of the perfusion of the medicament, at least two other axial positions are selected for imaging the perfusion. Accordingly, the pullback device incrementally withdraws the IVUS and pauses at a second position, a predetermined distance from the position of the first image. A second image is created at this second position. Once again, the pullback device is activated, and the IVUS is withdrawn to a third location along the artery. The imaging procedure is repeated, creating a third image. It can be appreciated that the clinician could select a greater number of sites depending on the specificity of the information desired. For instance, if images are created at increments of one to three millimeters along the artery at a given perfusion site, more than three images will be needed to observe the entire perfusion in detail. Consequently, the profile generated from the combined images will be more detailed than a corresponding profile generated from three images. In any event, the clinician can determine the number of images to be made based on observations of the image created at the first position. When the desired number of images has been made at the first infusion site, the IVUS is pulled back along the axis of the, artery. Accordingly, if additional infusions were made, a series of images is created at each infusion site. Upon the completion of the desired number of images at each location of perfusion, the IVUS is withdrawn from the artery.

In addition to creating images at specific sites along the inside of the artery, the present invention envisions using these images to quantify the results of the infusion. An important aspect of the present invention is an analysis of the profile created by the ultrasound. It is known that tissues with varying characteristics react differently to ultrasound radiation to produce images showing this variation. As noted above, the addition of a medicament to tissues changes the characteristics of the tissues containing the medicament for the purpose of creating an ultrasound image. Consequently, the tissues that contain the medicament will have a profile that differs from the profile of those tissues that do not contain the medicament. Based on this understanding, a quantitative analysis of the images can be performed to determine the relative amount of the medicament that has infiltrated into selected areas of tissue. Specifically, to accomplish this, data from the series of images is combined at an ultrasound/computer interface. It is known that each of the combined images-includes a radial and an azimuthal dimension of the perfusion. Accordingly, the composite of these images will yield a three dimensional image of each perfusion. Supported by these composite, three dimensional images, and the quantitative analysis of these images, a clinician can evaluate the pattern and the extent of the infiltration of the medicament.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
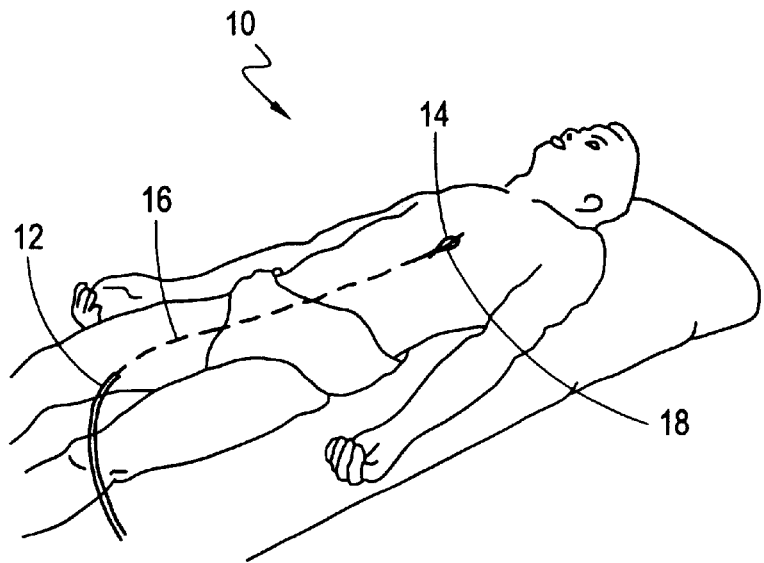
FIG. 1 is a perspective view of a patient with an IVUS positioned in an artery in accordance with the present invention.

Referring initially to FIG. 1, a system for determining the extent of an infiltration of an administered medicament is shown and generally designated 10. In accordance with the present invention, after an infusion procedure has been completed, a balloon catheter 12 housing an intravascular ultrasound device (IVUS) 14 is inserted into an artery 16 of a patient. The IVUS 14 is then advanced to an infusion site 18.

Figure 2:
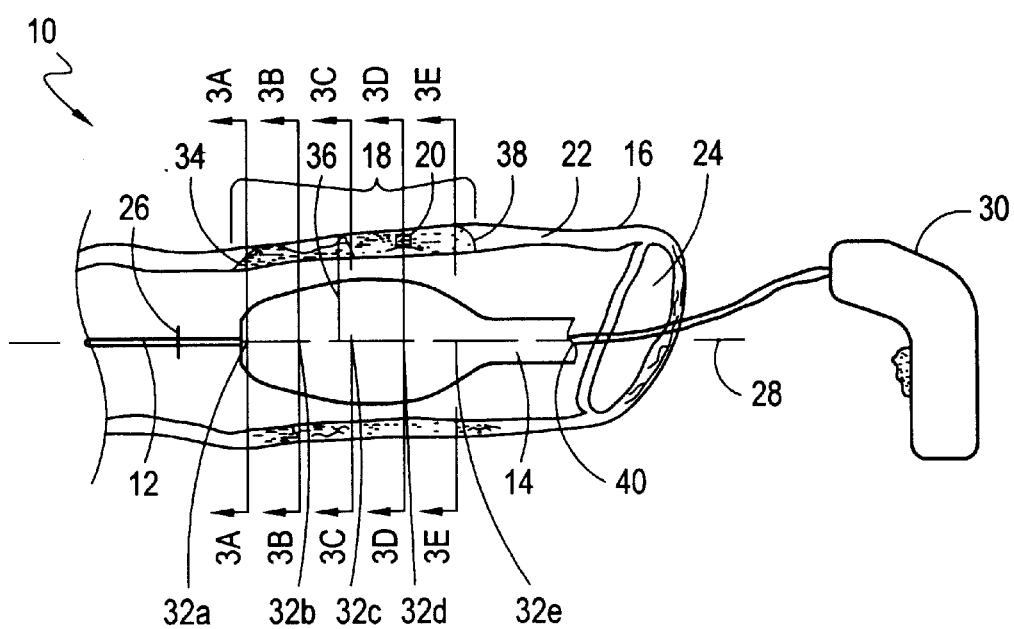
FIG. 2 is a cross sectional representation of an artery after an infusion, showing an intravascular ultrasound device positioned in the artery.

As shown in FIG. 2, the infused medicament 20 infiltrates into a tissue 22 surrounding an artery 16. The intravascular ultrasound device (IVUS) 14 is housed in a balloon catheter 12 in a manner well known in the art. It is also known that IVUS 14 images the tissue 22 surrounding the artery 16 from a position inside the artery 16. Upon insertion of the IVUS 14 into the lumen 24 of the artery 16, the IVUS 14 is advanced to a start point 26 therein. It is important to note that this start point 26 is distal to a first infusion site 18. When the clinician determines that this start point 26 is distal to the infusion site 18 that will be imaged, the IVUS 14 is activated. The IVUS 14 is then pulled back incrementally along the axis 28 of the artery 16, preferably using a motorized pullback device 30, in a manner well known in the art. Accordingly, the pullback device 30 incrementally withdraws the IVUS 14 and pauses at a position 32a, a predetermined distance from the start point 26. The IVUS 14 is activated at this position 32a, imaging the tissue 22 surrounding the artery 16. Once again the IVUS 14 is incrementally withdrawn and stopped at a third position 32b, whereupon it is activated to image the tissue 22 from this third axial position in the artery 16. As the IVUS 14 is thus pulled back along the axis 28 of the artery. 16, it is stopped and activated at preselected positions, for example 32b, c, d, and e.

It can be appreciated that it is desirable to know the boundaries of each perfusion of the medicament 20. These boundaries include a first end 34, a radius 36, and a second end 38. The radius 36 of the perfusion represents the depth of penetration of the medicament 20 into the tissue 22 surrounding the artery 16. In order to ascertain the boundaries of a perfusion, a number of axial positions 32 can be selected for imaging with the IVUS 14 at the infusion site 18. Inasmuch as the images created by IVUS 14 are formed at positions 32 along the axis 28 inside the artery 16, these boundaries will be represented by a radial and an azimuthal dimension. When the length of the infusion site 18 has been traversed, IVUS 14 reaches a stop position 40 for that infusion site 18. It follows that these determinations can be repeated for each infiltration that has been performed. Further, the IVUS 14 can be pulled back along the inside of the artery 16 and activated at a number of preselected positions 32a–e for each infusion site 18 to image each infiltration.

Figures 3A, 3B, 3C, 3D, 3E:
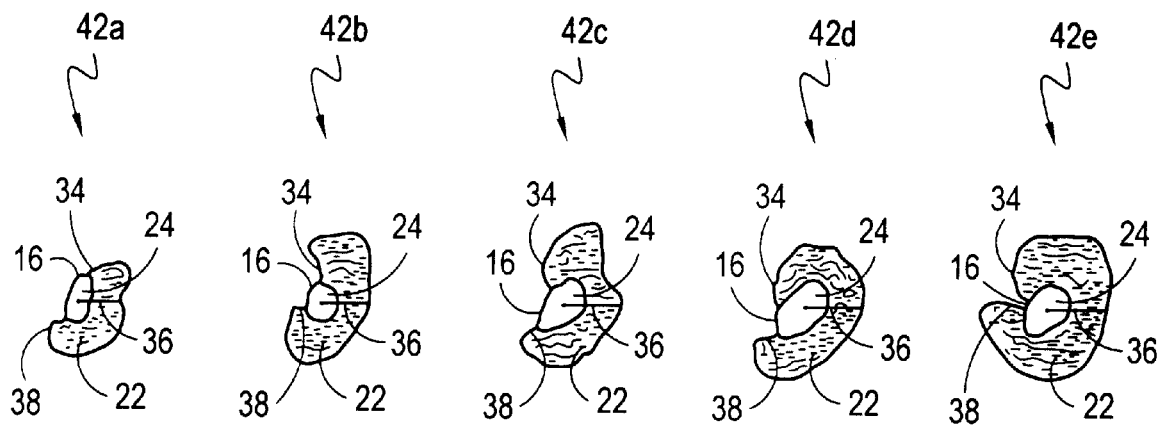
FIGS. 3A–3E are respective cross sectional views of the infusion of a medicament as would be seen at locations in an artery respectively indicated by lines 3A—3A, 3B—3B, 3C—3C, 3D—3D, and 3E—3E in FIG. 2.

As shown in FIGS. 3A–3E, it is contemplated that a number of images 42a–e will be created at a given infusion site 18. It follows that, if a medicament 20 has been infused at more than one infusion site 18, each infusion site 18 will be imaged a number of times. Accordingly, the number of images 42 required at each infusion site 18 can be determined depending on the specificity of the information desired. For instance, if images 42 are created at increments of one to three millimeters along the artery 16 at a given infusion site 18, several images 42 will be needed to observe the entire perfusion in detail. Consequently, the profile generated from these combined images 42 will be more detailed than a corresponding profile generated from a minimal three images 42. In any event, the clinician can select the number of images to be made based on observations of the image 42 created at the first position 32a, and on the specificity of the information desired. It can be appreciated that each image 42 thus created will represent the extent of the medicament 20 which has infiltrated the tissue 22 surrounding the artery 16 at each specific position, for example 32a–e. FIGS. 3A, 3B, 3C, 3D, and 3E correspond to images 42a–e. These images 42a–e, in turn, are cross sectional views, created by IVUS 14 at positions 32a–e along the axis 28 of the artery 16. For example, FIG. 3A shows image 42a, as would be seen along the line 3A—3A in FIG. 2. It follows that FIG. 3B shows image 42b as would be seen along the line 3B—3B. Thus, each image 42 represents a cross sectional view as imaged by IVUS 14 from a specific position 32 along the axis 28 of the artery 16. Each image 42 that is created at each position 32 along the axis 28 will show a first end 34, a radius 36, and a second end 38. Further, these cross sectional images 42 will each include an azimuthal dimension. When the desired number of images 42 has been made at the first infusion site 18, the IVUS 14 is pulled back along the axis 28 of the artery 16. Accordingly, if additional infusions have been performed, the IVUS 14 pauses at a second infusion site 18 to create a second series of images 42 in the same manner as the first series of images 42 was made. It follows that a series of images 42 can be created at each infusion site 18. Upon the completion of the desired number of images 42 at each infusion site 18, the IVUS 14 is withdrawn from the artery 16.

Figure 4:
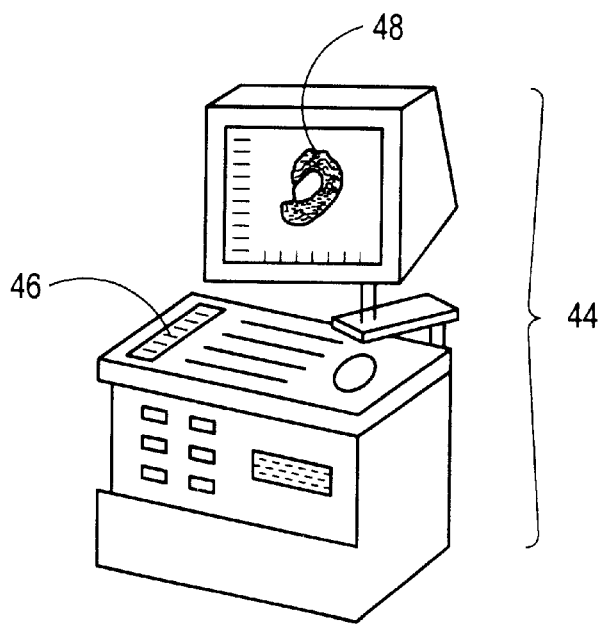
FIG. 4 is a perspective view of a computer/ultrasound interface in accordance with the present invention.

FIG. 4 shows a computer/ultrasound interface 44. In addition to creating images 42 at specific positions 32 for each infusion site 18 along the artery 16, the present invention envisions using these images 42 to quantify the results of the infusion. To that end, the present invention contemplates integrating data from IVUS 14 at this interface 44. The computer 46 at this interface 44 combines the images 42, created by IVUS 14 at each infusion site 18 to create three dimensional images 48 of each infusion site 18, indicating a profile of the infiltration of the medicament 20 at that infusion site 18. Each image 42 is formed by the IVUS 14 at a specific axial position 32. Since it is known that each of the images 42 includes a radial and an azimuthal dimension of the perfusion, it follows that the composite of these images 42 for each infusion site 18 will yield a three dimensional image 48 of each perfusion.

Another important aspect of the present invention is a quantitative analysis of the profile created by the IVUS 14. This analysis can be performed by the computer 46 at the computer/ultrasound interface 44 to provide further details of the extent of the infiltration of the medicament 20 into the tissue 22 surrounding the artery 16. As discussed above, the addition of a medicament 20 to tissues 22 changes the characteristics of the tissues 22 containing the medicament 20 for the purpose of creating an ultrasound image 42. Consequently, the tissues 22 that contain the medicament 20 will have a profile that differs from the profile of those tissues 22 that do not contain the medicament 20. Based on this understanding, a quantitative analysis of the images 42 can be performed to determine the relative amount of the medicament 20 that has infiltrated into selected areas of the tissue 22. Supported by the composite, three dimensional images 48, and the quantitative analysis of these composite images 48, a clinician can evaluate the pattern and the extent of the infiltration of the medicament 20.

While the particular methods and systems for ultrasonically profiling the infiltration of an administered medicament into the arterial wall of a patient as herein shown and disclosed in detail are fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for determining the extent of an infiltration of medicament at a location of infusion of the medicament into an arterial wall of a patient comprising the steps of:

advancing an intravascular ultrasound device into an artery of the patient to a start position, said start position being distal to said location of infusion;

incrementally withdrawing said intravascular ultrasound device in a proximal direction from said start position to at least one other position in the artery; and activating said ultrasound device at each said position in the artery, to create a profile for the infiltration of said medicament into the arterial wall at each said position.

2. A method as recited in claim 1 wherein the artery substantially defines a longitudinal axis at said location of infusion and each said profile includes a radial dimension and an azimuthal dimension relative to said axis.

3. A method as recited in claim 2 wherein said ultrasound device generates dimensional data indicating each said profile and said method further comprises the step of using a computer to evaluate said data, wherein said computer further forms a three dimensional image representing a composite of said plurality of profiles.

4. A method as recited in claim 1 wherein said withdrawing step is accomplished using a mechanical pullback device.

5. A method for modeling a volume of medicated tissue along an artery in a patient, said tissue being infused with a fluid medicament, comprising the steps of:

radiating the medicated tissue with ultrasound energy at a location in the artery to generate data indicative of a profile of the medicated tissue;

repeating said radiating step at other said locations in the artery to generate data for a plurality of said profiles; and combining data from said plurality of profiles to create a three-dimensional model of the medicated tissue.

6. A method as recited in claim 5 wherein said radiating step is accomplished using an intravascular ultrasound device.

7. A method as recited in claim 6 wherein said intravascular ultrasound device generates dimensional data indicating each said profile and said method further comprises the step of using a computer to evaluate said data of said profile.

8. A method as recited in claim 5 wherein the artery defines a longitudinal axis at each said location, each said profile includes a radial dimension and an azimuthal dimension relative to said axis.

9. A method as recited in claim 5 wherein said repeating step is accomplished using a mechanical pullback device.

10. A system for evaluating an infiltration of a medicament into tissue surrounding an artery of a patient at a location in the artery which comprises:

a means for radiating the infiltration with ultrasound energy to generate data indicative of a profile of the infiltration into the tissue surrounding the artery at said location; and a means for evaluating said data to determine the extent of the infiltration.

11. A system as recited in claim 10 wherein said means for radiating the tissue surrounding the artery is an intravascular ultrasound device.

12. A system as recited in claim 11 wherein said intravascular ultrasound device generates data indicative of a plurality of profiles at a plurality of locations in the artery.

13. A system as recited in claim 12 wherein said intravascular ultrasound device interfaces with a computer to create a three dimensional model of the tissue surrounding the artery.

14. A system as recited in claim 12 wherein said intravascular ultrasound device is incrementally withdrawn from the artery to generate said plurality of profiles.

15. A system as recited in claim 14 wherein said ultrasound device is incrementally withdrawn from the artery using a mechanical pullback device.

16. A system as recited in claim 10 wherein the artery defines a longitudinal axis at said location, said profile includes a radial dimension and an azimuthal dimension relative to said axis.

* * * * *